United States Patent [19]

Yamaguchi et al.

[11] 4,206,173
[45] Jun. 3, 1980

[54] GAS COMPOSITION SENSOR

[75] Inventors: Hiroaki Yamaguchi, Anjo; Tadashi Hattori, Okazaki; Siniti Yamamoto, Takahama, all of Japan

[73] Assignee: Nippon Soken, Inc., Nishio, Japan

[21] Appl. No.: 903,659

[22] Filed: May 8, 1978

[30] Foreign Application Priority Data

May 13, 1977 [JP] Japan .................................. 52-55781

[51] Int. Cl.² ........................................ G01N 31/10
[52] U.S. Cl. .................................. 422/98; 73/27 R; 338/34
[58] Field of Search ................... 73/26, 27 R; 338/34, 338/333; 422/98

[56] References Cited

U.S. PATENT DOCUMENTS

| | | | |
|---|---|---|---|
| 2,812,409 | 11/1957 | Jones et al. ................... | 338/333 X |
| 2,950,996 | 8/1960 | Place, Sr. et al. ................ | 338/333 |
| 3,051,895 | 8/1962 | Carson ......................... | 324/71 R |
| 3,550,057 | 12/1970 | Young ........................... | 338/34 |
| 3,564,474 | 2/1971 | Firth et al. .................... | 73/27 R |
| 3,603,954 | 9/1971 | Takeuchi ........................ | 73/26 X |
| 3,676,820 | 7/1972 | Taguchi ......................... | 73/27 R |
| 3,865,550 | 2/1975 | Bott et al. ..................... | 338/34 X |
| 3,932,246 | 1/1976 | Stadler et al. .................. | 73/27 R |
| 3,959,765 | 5/1976 | Stewart ......................... | 338/34 |
| 4,013,943 | 3/1977 | Chou et al. ..................... | 340/634 X |
| 4,029,472 | 6/1977 | Micheli et al. .................. | 73/26 X |
| 4,030,340 | 6/1977 | Chang ........................... | 73/26 X |
| 4,066,413 | 1/1978 | Segawa et al. ................... | 422/98 |

*Primary Examiner*—Daniel M. Yasich
*Attorney, Agent, or Firm*—Cushman, Darby & Cushman

[57] ABSTRACT

A gas composition sensor for sensing the air-fuel ratio of the exhaust gases from an automobile. The gas composition sensor includes a gas composition sensing element composed of a sintered metal oxide having an electric resistance value varying in accordance with the composition of gases to be sensed, and at least one reticulated metal plate is disposed inside or on the surface of the gas composition sensing element.

13 Claims, 24 Drawing Figures

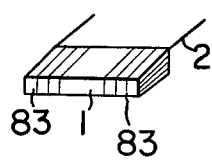
FIG.12
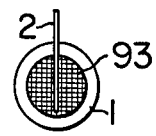
FIG.13(a)
FIG.13(b)
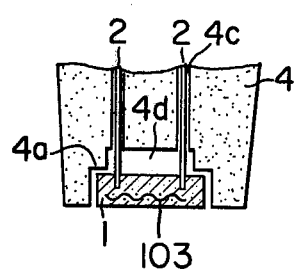
FIG.14
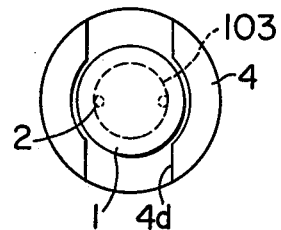
FIG.15
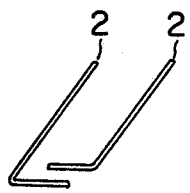
FIG.16
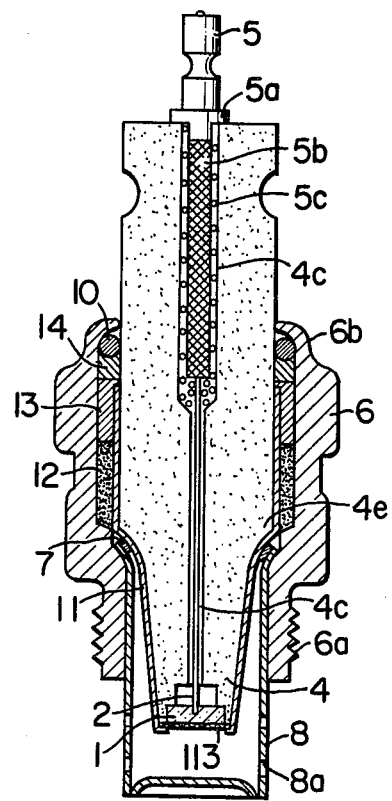
FIG.17

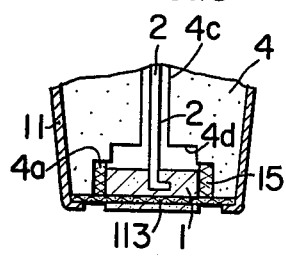
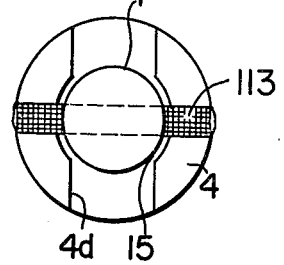
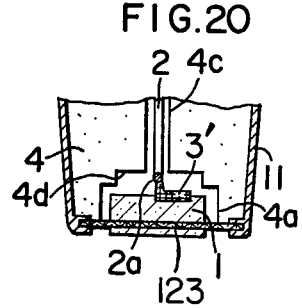
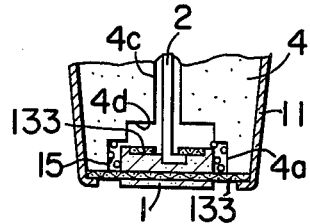
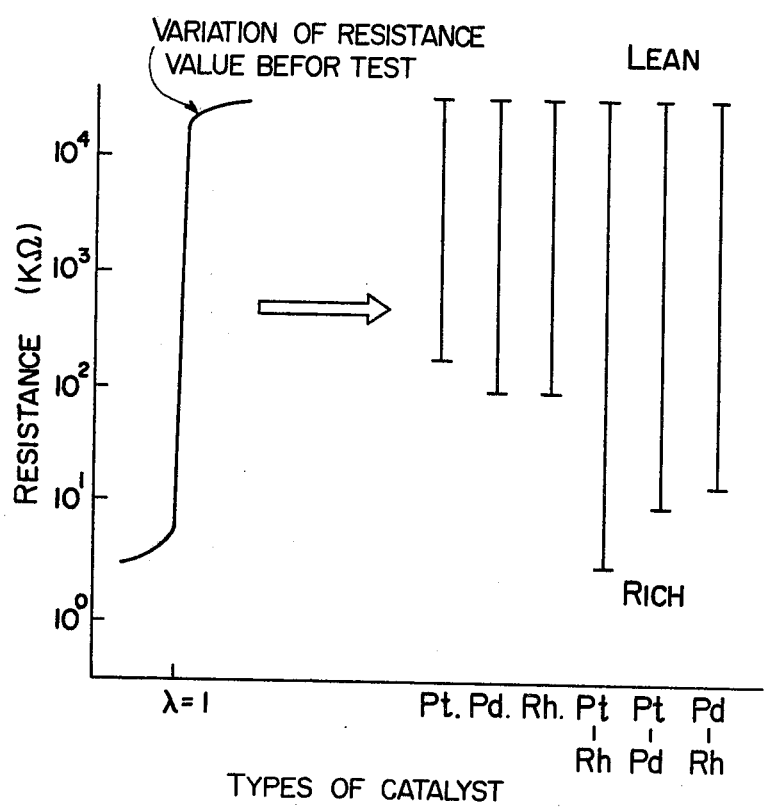

GAS COMPOSITION SENSOR

BACKGROUND OF THE INVENTION

1. Field of the Invention

The present invention relates to gas composition sensors for sensing the air-fuel ratio of the exhaust gases from automobiles, for example.

2. Description of the Prior Art

Recently, in connection with the control of objectionable emissions from internal combustion engines, gas composition sensors have been in use as a means of sensing the air-fuel ratio of mixtures supplied for burning in an engine. In other words, where an exhaust gas purifying catalyst is employed as a means of controlling objectionable emissions from an engine, the air-fuel ratio of mixtures must always be maintained at a proper value in order to allow the catalyst to give full play to its capacity. However, with the carburetors of the ordinary engines or with the fuel injection systems of the fuel injection engines, even if the carburetor or the injection system is adjusted so that the air-fuel ratio of mixture is maintained at a predetermined value, the air-fuel ratio will in fact be varied greatly. As a result, in order that the air-fuel ratio of mixture may be maintained constant, the actual air-fuel ratio must be sensed by some means or other to feedback the resulting detection signal to the carburetor or the injection system.

The gas composition sensor senses the air-fuel ratio by utilizing the fact that the variation in the concentration of the exhaust gas composition is directly related closely to the air-fuel ratio of mixture.

In the past, to sense variation in the concentration of the composition of exhaust gases to be sensed, a gas composition sensing element comprising a transition metal oxide with a catalytic layer deposited on its outer surface has been used to sense the variation in the concentration by sensing the variation in the electric resistance value of the element, and the catalytic layer has the function of improving the sensitivity of the transition metal oxide to variation in the concentration of the exhaust gas composition. The use of such catalytic layer has been proposed by the present assignee by U.S. Patent Application of Hattori et al, Ser. No. 850,032, now abandoned, which was filed on Nov. 9, 1977.

Although the response of the gas composition sensing element to variation in the exhaust gas composition can be improved with decrease in the thickness of the gas composition sensing element, the strength of the gas composition sensing element will be reduced with decrease in its thickness, thus making it difficult to improve its response to an extreme extent.

SUMMARY OF THE INVENTION

It is an object of the invention to provide a gas composition sensor including a gas composition sensing element having an improved response and reduced in thickness.

It is another object of the invention to provide a gas composition sensor including a gas composition sensing element having a reduced thickness and increased strength.

It is still another object of the invention to provide a gas composition sensor including a gas composition sensing element which bears or envelopes at least on reticulated metal plate.

BRIEF DESCRIPTION OF THE DRAWINGS

FIG. 3 is a bottom plan view of FIG. 2a.

FIG. 12 is a perspective view showing still another form of the gas composition sensing element section.

FIGS. 13(a) and 13(b) are a front view and a plan view showing still another form of the gas composition sensing element section.

FIG. 14 is a sectional view showing in detail the construction of the gas composition sensing element in another embodiment of the invention.

FIG. 15 is a bottom view of FIG. 14.

FIG. 16 is a perspective view showing a form of the electrode arrangement.

FIG. 17 is a sectional view showing the overall construction of still another embodiment of the invention.

FIG. 18 is a sectional view showing in detail the construction of the gas composition sensing element section shown in FIG. 17.

FIG. 19 is a bottom view of FIG. 18.

FIGS. 20 and 21 are sectional views similar to FIG. 18, showing still another embodiments of the invention.

FIG. 22 shows changes of resistance values of various sensing elements when they are used in the embodiments shown in FIGS. 17 to 19.

DESCRIPTION OF THE PREFERRED EMBODIMENTS

Figure 1:
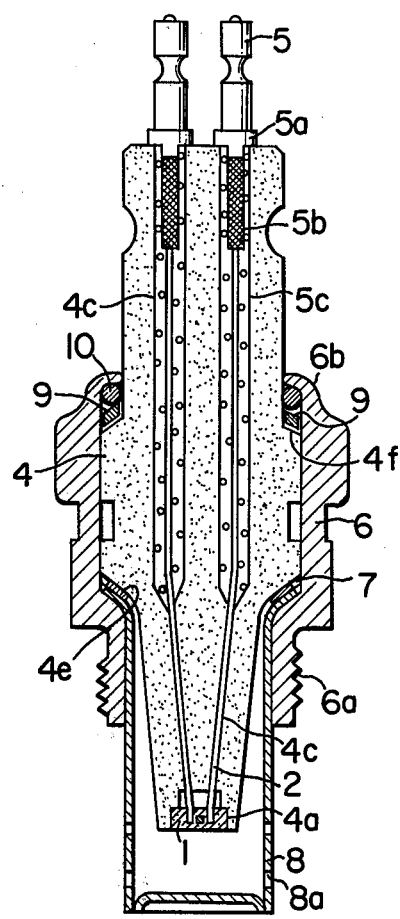
FIG. 1 is a sectional view showing the overall construction of an embodiment of a gas composition sensor according to the invention.
Figure 2A:
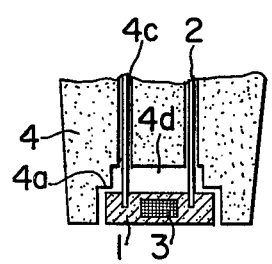
FIG. 2(a) is a sectional view showing in detail the construction of the gas composition sensing element section shown in FIG. 1.
Figure 3:
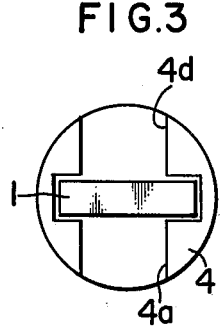
Figure 2B:
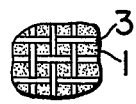
FIG. 2(b) is a fragmentary sectional view on an even larger scale, of the sensing element and metal plate of FIG. 2.
Figure 4:
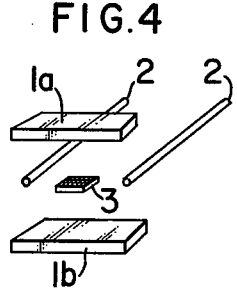
FIG. 4 is a perspective exploded view of the gas composition sensing element section shown in FIGS. 1 to 3.

Referring to FIGS. 1 to 3, numeral 1 designates a gas composition sensing element in the form of sintered sheets of a transition metal oxide or other metal oxide such as tin oxide whose electrical resistance varies in accordance with the composition of gases such as oxygen, and a pair of electrodes 2 made of platinum or the like have their one ends embedded in the sensing element 1. The pair of electrodes 2 are provided to detect variations in the electric resistance value indicated by the gas composition sensing element 1. Briefly, the manufacturing process of the gas composition sensing element 1 comprises the steps of forming a slurry by milling in a ball mill 50% by weight of titanium oxide (TiO$_2$) powder stabilized by preliminary sintering, 40% by weight of an organic solvent, 5% by weight of a binder and 5% of a plasticizer, forming a large number of sheets of about 0.2 mm thick by means of the doctor blade process and laminating the sheets to adjust the thickness of laminated sheets. These multiple laminated sheets are designated by numerals 1a and 1b in FIG. 4. After the ends of the electrodes 2 have been placed, along with a reticulated platinum (Pt) body in the form of a plate 3, between the sheets 1a and 1b thus forming a sandwich structure, the structure is compressed so that the plate 3 bites into the sensing element, formed and then sintered at a temperature between 800° and 1,200° C. The reticulated plate 3 is arranged so as not to produce a short-circuit between the electrodes 2. The gas composition sensing element 1 has a rectangular cross-sectional shape. Numeral 4 designates a holding member made of a heat-resisting and electrically insulating metal oxide such as alumina, and it is formed in one end with a stepped recess 4a. The sensing element 1 is received in the stepped recess 4a. The pair of electrodes 2 embedded in the sensing element 1 are inserted into holes 4c extending through the holding member 4, more particularly into the holes 4c in the lower portion of the holding member 4. Inserted into the holes 4c in the upper portion of the holding member 4 are a pair of lead wires 5 each having a collar 5a and a knurled portion 5b. A sealing is provided between the holding member 4 and the lead wires 5 at the knurled portions 5b by means of a glass ceramic cement material 5c, for example. The electrodes 2 are electrically connected to the lead wires 5. Numeral 4d designates a transverse slot 4d formed to allow exhaust gases to contact the sensing element 1 from both the upper and lower surfaces thereof, and the transverse slot 4d is defined by the stepped recess 4a to radially extend through the holding member 4. Numeral 6 designates a housing of a heat resisting metal having a threaded portion 6a for fitting in the exhaust pipe. Fitted on a lower tapered portion 4e of the holding member 4 is a protective cover 8 made of a heat resisting metal and having a heat resisting metal washer 7 and holes 8a through which the exhaust gases can pass, and also fitted on an upper tapered portion 4f are a ring 9 and a washer 10 which are made of a relatively soft metal (e.g., copper). An upper portion 6b of the housing 6 is caulked to be bent inwardly thus firmly fastening the holding member 4 and the housing 6 together.

With the construction described above, the gas composition sensor is fixedly mounted to the exhaust pipe (not shown) by means of the housing 6. The electric resistance value of the sensing element 1 of the sensor varies in response to variation in the concentration of the components (CO, HC, H$_2$, O$_2$, etc.) of the exhaust gases passing through the exhaust pipe. The resulting electric signal from the sensing element 1 is taken off by the lead wires 5 through the electrodes 2, and the signal is applied to a control circuit. As is well known, the exhaust gas is composed of such components as O$_2$, NOx, CO, HC, H$_2$, etc., and the concentrations of these components vary in dependence on the air-fuel ratio of the mixture before combustion. The gas composition sensing element 1 is principally responsive to the concentration or partial pressures of O$_2$, CO and HC of these components, and moreover the electric resistance value of the sensing element 1 varies in response to variation in the overall atmosphere produced by these components rather than variation in the partial pressure of the individual components. The value of the electric resistance is also affected by the temperature of the exhaust gases and it varies in response to the temperature. The components of the exhaust gas penetrate into the porous gas composition sensing element 1 and the catalytic action of the reticulated Pt plate 3 promotes such reactions as $CO + \frac{1}{2}O_2 \rightarrow CO_2$, $HC + XO_2 \rightarrow YCO_2 + ZH_2O$, etc. As a result, in the portion of the gas composition sensing element 1 including the reticulated Pt plate 3, the response of the gas composition sensing element 1 to the partial pressure of O$_2$ in the gas components contacting it is increased and consequently its electric resistance is varied rapidly in response to variation in the partial pressure of O$_2$.

In this connection, the response of the gas composition sensing element 1 is determined by the thickness of the sensing element itself, although it is also dependent on the reticulated Pt plate 3. While the response of the sensing element 1 can be improved with decrease in its thickness, its strength decreases with decrease in the thickness. With the present embodiment, however, by virtue of the fact that the Pt sheet 3 disposed inside the gas composition sensing element 1 is reticulated, as for example, the sheets 1a and 1b of FIG. 4 contact with each through the reticulation of the Pt plate 3 in its vicinity with the resulting increase in the adhesion strength of the gas composition detecting element 1, and consequently even if the thickness of the gas composition sensing element 1 is decreased correspondingly, practically there will be, for example, no danger of the sheets 1a and 1b separating from each other. In addition, even if the gas composition sensing element 1 is cracked so that it tends to be broken, by virtue of the fact that the gas composition sensing element 1 bears or encloses the Pt plate 3, the sensing element portion including the reticulated Pt plate 3 is hard to be broken, and consequently even if the thickness of the gas composition sensing element 1 is decreased, practically there will be no danger of reduction in the strength of the sensing element 1.

While, as is well known, the temperature of the exhaust gases frequently rises to an extreme extent, since the reticulated Pt plate 3 is disposed inside the gas composition sensing element 1 so that it is not directly subjected to the heat of the exhaust gases, the catalytic performance of the reticulated Pt plate 3 can be stably maintained over a long period of time. Also, by virtue of the fact that the gas composition sensing element 1 is enclosed by and cemented to the inner walls of the recess 4a of the holding member 4 excluding the side exposed to the exhaust gases, when the detector is vibrated, the tendency of the gas composition detecting element 1 to move under the force of the vibrations is opposed by the inner walls of the recess 4 of the holding member 4, thus preventing the movement of the gas composition sensing element 1 due to the vibrations. Thus, an improved resistance to vibrations is ensured for the mounting and holding structure of the sensing element 1 on the holding member 4.

Further, since the gas composition detecting element 1 is received in the recess 4a of the holding member 4, the thickness of the gas composition sensing element 1 can be decreased by reducing the depth of the recess 4a of the holding member 4. The reduced thickness of the gas composition sensing element 1 has the effect of improving the response of the gas composition sensing element 1 to variation in the concentration of the gas composition.

Figure 5:
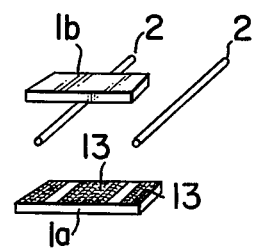
FIG. 5 is a perspective exploded view showing another form of the gas composition sensing element section.

FIG. 5 shows another form of the gas composition sensing element obtained by preparing two sheets 1a and 1b of metal oxide (e.g., TiO₂), preparing a thickly reticulated Pt plate 13 by preliminarily spreading and baking a Pt paste and placing it on one of the sheets, i.e., the sheets 1a excluding those portions where electrodes are to be inserted, inserting and arranging the ends of electrodes 2 between the sheets 1a and 1b and then sintering the assembly. In this form of the sensing element 1, the reticulated Pt plate 13 consists of Pt and a virtreous or ceramic material and it is in the form of a thick and rigid plate.

Figure 6:
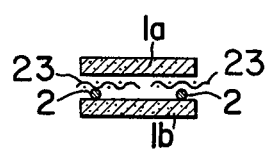
FIGS. 6 and 7 are exploded sectional views showing still another forms of the gas composition sensing element section.

FIG. 6 shows still another form of the gas composition sensing element section in which two reticulated Pt plates 23 are disposed inside the sensing element 1 (interposed between sheets 1a and 1b) so as to contact with electrodes 2, and its manufacturing process is the same as the element of FIG. 5. Also, in this form, the Pt plates 23 must be arranged not to cause a short-circuit between the electrodes 2.

Figure 7:
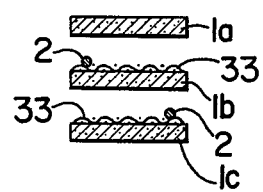

FIG. 7 shows still another form of the gas composition sensing element section obtained by preparing three sheets 1a, 1b and 1c of metal oxide, placing a reticulated Pt plate 33 on each of the sheets 1b and 1c, inserting and arranging the end of an electrode 2 between the sheets 1a and 1b and between the sheets 1b and 1c, respectively and then sintering the assembly.

Figure 8:
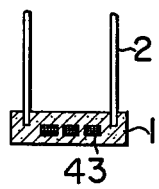
FIG. 8 is a sectional view showing still another form of the gas composition sensing element section.

FIG. 8 shows still another form of the gas composition sensing element 1 in which three reticulated Pt plates 43 are disposed inside the sensing element 1, and its manufacturing process is the same as the element shown in FIG. 5.

Figure 9:
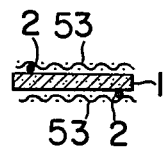
FIG. 9 is an exploded sectional view showing still another form of the gas composition sensing element section.

FIG. 9 shows still another form of the gas composition sensing element section in which an electrode 2 and a reticulated Pt plate 53 are arranged on each side of a sheet 1 constituting the sensing element 1 so as to press each electrode 2 in place by the associated Pt plate 53 and then the assembly is sintered.

Figure 10:
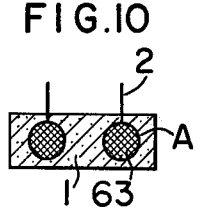
FIG. 10 is a sectional view showing still another form of the gas composition sensing element section.

FIG. 10 shows still another form of the gas composition sensing element section in which a part of each electrode 2 consists of a reticulated Pt plate 63, that is, the reticulated Pt plate 63 is made integral with the electrode 2 by connecting it to the latter by spot welding at a point A, and in this case the reticulated Pt plate 63 serves to prevent the electrode 2 from slipping out of position.

Figure 11:
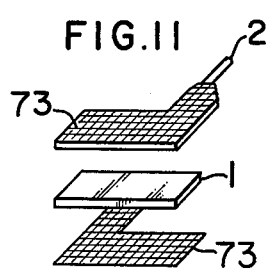
FIG. 11 is a perspective exploded view showing still another form of the gas composition sensing element section.

FIG. 11 shows still another form of the gas composition sensing element section in which a part of each reticulated Pt plate 73 is formed into an electrode 2, and in this case there is no need of connection by spot welding.

FIG. 12 shows still another form of the gas composition sensing element section in which Pt wires are wound on the outer surface of a gas composition sensing element 1 in a reticulate arrangement to form Pt members 83 and an electrode 2 is fixed by welding to the terminal end of each wound Pt wire. In this case, the electrodes 2 may of course be embedded within the gas composition sensing element 1.

FIG. 13 shows still another form of the gas composition sensing element section in which a disk-shaped reticulated Pt plate 93 is disposed to press an electrode 2 against each side of a gas composition sensing element 1 in the form of a thin disk.

FIGS. 14 and 15 show still another form of the gas composition sensing element section in which a gas composition sensing element 1 is in the form of a disk and a reticulated Pt plate 103 is also in the form of a disk.

Also, as shown in FIG. 16, the ends of the electrodes 2 in FIGS. 2a and 8 may be bent to allow the electrodes 2 to serve as catalysts.

On the other hand, it is of course possible to cement the outer periphery of the gas composition sensing element 1 to the recess 4a of the holding member 4 by means of an inorganic cementing material such as borosilicate glass. In this case, the cementing may be accomplished by a metal oxide of the same material as the gas composition sensing element 1. The cementing effect may be improved by forming the metal oxide into a slurry, applying the slurry to the portions to be cemented and then burning the slurry. This has the effect of preventing deterioration of the gas composition detecting element 1 by the components (Pb, Fe, etc.) contained in the ordinary cementing material.

On the other hand, by forming a porous film of a metal oxide (e.g., alumina) on the surface of the gas composition sensing element 1 exposed to the exhaust gases to be detected, it is possible to protect the gas composition sensing element 1 from the impurities (Pb, Fe, S, etc.) in the exhaust gases to be detected.

Further, while the metal oxide is TiO₂ in the previously mentioned embodiments, other metal oxide, such as, NiO, CoO, MnO, ZnO, CuO or SnO₂ may also be used.

Further, while, in the above-described embodiments, the reticulated metal member is a so-called reticulated Pt plate, a punched plate obtained by forming a large number of holes in a reticulate arrangement in a Pt plate may also be used, and it is also possible to use a plurality of Pt rods in a reticulate arrangement.

FIGS. 17 to 19 show still another embodiment of the invention in which a reticulated Pt sheet 113 also serves as an electrode. In this embodiment (the construction of the electrode conductor path in the gas composition sensor shown in FIG. 17 is disclosed in U.S. Patent Application of Hallori et al Ser. No. 853,839, filed on Nov. 21, 1977 now U.S. Pat. No. 4,130,797, issued Dec. 19, 1978, a thin-film Pt conductor path 11 is formed in a holding member 4 (along the outer surface thereof) to electrically connect a Pt plate 113 serving as an electrode to a housing 6, and the conductor path 11 is electrically connected with the housing 6 by way of a conductive powder 12 consisting of black lead or the like and placed in the space between the housing 6 and the holding member 4. Consequently, the Pt plate 113 is connected to the housing 6 through the conductor path 11 and the conductive powder 12. Numeral 13 designates a stainless steel spacer, 14 a nickel ring, and 15 a cement.

A hole 4c is formed in the holding member 4 through which an electrode 2 extends to electrically connect one side of the sensing element 1 with a lead terminal 5 at a lower portion thereof. The terminal 5 is formed with a collar 5a as in the embodiment shown in FIG. 1, as well as a knurled portion 5b inserted into the upper portion of the hole 4c. A cementing material 5c is filled in the space between the holding member 4 and the terminal 5 to fixedly secure the terminal in the holding member 4 and assure the electrical connection between the electrode 2 and the terminal 5. Other portions in FIGS. 17 to 19 designated by the same numerals used in FIGS. 1 to 3 show the same or equivalent portions, respectively.

While, in the embodiment described above, the metal adapted to serve a catalytic function is Pt, the metal is not limited to Pt, and Pd or Rh or the mixtures of Pt, Pd, and Rh may also be used.

FIG. 22 shows the changes, after the endurance tests, in the resistance value of the gas composition sensing element 1 in the embodiment of FIGS. 17 to 19 employing the sheet 3 (acting as one electrode) consisting of Pt, Pd, Rh, Pt-Rh, Pt-Pd and Pd-Rh, respectively.

In FIG. 22, the Z-shaped curve shows the variation in the resistance value of the element 1 before the tests in relation to the excess air factor. The six bar lines in the right portion of FIG. 22 represent the range of changes in the resistance value of the element 1 after the endurance tests conducted under the conditions indicated in the Figure, and the bar lines indicate, from the left to the right, the range of changes corresponding to the Pt, Pd, Rh, Pt-Rh, Pt-Pd and Pd-Rh plates, respectively.

As will be seen from this graph, it has been concluded that the sheet 3 consisting of the Pt-Rh metal showed practically the same range of changes in the resistance value before and after the tests thus proving that the Pt-Rh metal is the most desirable material for the plate 3.

FIG. 20 shows still another embodiment of the invention which differs from the embodiment of FIGS. 17 to 19 in that a reticulated Pt wire 3' is welded to the forward end 2a of the electrode 2, and a part of the Pt wire 3' is embedded in the gas composition sensing element 1.

FIG. 21 shows still another embodiment of the invention which differs from the embodiment of FIGS. 17 to 19 in that reticulated Pt plates 133 are attached by contact bonding to the electrode 2 side of the gas composition sensing element 1. In the embodiments shown in FIGS. 17 to 21, the gas composition sensing element 1 is in the form of a disk. Of course, the detecting element 1 may be in the form of a square cylinder.

It will thus be seen that with the embodiment shown in FIGS. 17 to 19, the holding member 4 needs not be formed with a pair of passages for the electrodes 2 as in the case of FIG. 1, and only a single hole through the holding member 4 is needed thus making the manufacture of the holding member 4 very easy.

Further, with this embodiment, the fact that one of the electrodes (the Pt plate 133 serves as the electrode) is connected to the conductor path 11 through the reticulated Pt plate 133, has the effect of ensuring an electric connection between the electrodes and the conductor path.

It will thus be seen from the detailed description of the invention that the device of this invention has among its great advantages the fact that at least one reticulated metal is firmly supported on a gas composition detecting element with the result that the holding strength of the reticulated metal on the gas composition detecting element is reinforced by the reticulation of the reticulated metal and at the same time a part of the gas composition sensing element bites the reticulation, thus practically eliminating the danger of a reduction in the thickness of the gas composition sensing element resulting in a reduction in strength and improving the response of the gas composition sensing element without bringing about a reduction in strength.

We claim:

1. A gas composition sensor, comprising:
    a gas composition sensing element of plate shape consisting of at least one body of sintered metal oxide having an electric resistance value varying in accordance with variation of the composition of a gas to be sensed;
    at least one reticulated metal body in the form of a sheet fixedly held by said gas composition sensing element as by compressing said gas sensing element and said reticulated metal body such that said reticulated metal sheet bites said sintered metal oxide to provide close adhesion between said metal sheet and said sintered metal oxide; and
    two electrodes, each one of them having one end thereof fixed to said gas composition sensing element to take off and thus permit detection of the electric resistance value indicated by said gas composition sensing element when said gas composition sensing element is exposed to such gas;
    said at least one reticulated metal body not electrically connecting the two electrodes to one another; and
    said at least one reticulated metal body being composed of at least one metal having a catalytic nature of improving the sensitivity of the metal oxide of said gas composition sending element to variation in concentration of at least one component of said gas,
    whereby said reticulated sheet gives a reinforcing strength to said gas composition sensing element of plate shape to allow said sensing element to have a reduced thickness thereby providing said sensing element with a high response as well as an increased strength.

2. A gas composition sensor as set forth in claim 1, wherein:
    said at least one reticulated metal body is made integral with the said one end of at least one of said electrodes.

3. A gas composition sensor as set forth in claim 1 or 2, wherein:
    said at least one reticulated metal body consists of a wire of noble metal capable of oxidizing at least one component of said gas to be sensed.

4. A gas composition sensor as set forth in claim 1, wherein:
    said reticulated metal sheet is connected to one of said two electrodes and serves as one of said electrodes.

5. A gas composition sensor as set forth in claim 1, wherein:
    said gas composition sensing element comprises a plurality of metal oxide sheets, and wherein said electrodes and said at least one reticulated metal body are disposed among said metal oxide sheets and form a sandwich structure therewith.

6. A gas composition sensor as set forth in claim 1, wherein:
    said at least one reticulated metal body and one of said electrodes are respectively fixed to superficial faces of said gas composition sensing element.

7. A gas composition sensor as set forth in claim 1 wherein:
    said at least one reticulated metal body is disposed and mounted inside said gas composition sensing element.

8. A gas composition sensor, comprising:
    a gas composition sensing element of plate shape consisting of at least two sheets of sintered metal oxide having an electric resistance value varying in accordance with variation of the composition of a gas to be sensed;
    two reticulated metal sheets;

two electrodes, each one of them having one end thereof contacting a respective one of said two reticulated metal sheets;

said two reticulated metal sheets being sandwiched between said at least two sheets of sintered metal oxide such that said reticulated metal sheets bite said two sheets of sintered metal oxide to provide close connection between said two sheets of sintered metal oxide through said reticulated metal sheets, with said two reticulated metal sheets not in electrical contact with one another;

both of said two reticulated metal sheets being composed of at least one metal having a catalytic nature of improving the sensitivity of the metal oxide of said gas composition sensing element to variation in concentration of at least one component of said gas, whereby said reticulated metal sheets give a reinforcing strength to said gas composition sensing element of plate shape to allow said sensing element to have a reduced thickness thereby providing said sensing element with a high response as well as an increased strength.

9. A gas composition sensor, comprising:

a gas composition sensing element of plate shape consisting of at least one body of sintered metal oxide having an electric resistance value varying in accordance with variation of the composition of a gas to be sensed;

two portions of metal wire separated from each other and fixedly wound on an outer surface of said gas composition sensing element in a reticulate arrangement such that said metal wire bites said outer surface of said sensing element to provide close adhesion between said metal wire and said sintered metal oxide;

two electrodes each one of them having one end thereof electrically connected and fixed to respective one of said two portions of metal wire to take out and thus permit detection of the electric resistance value indicated by said gas composition sensing element when said gas composition sensing element is exposed to such gas; and said two portions of metal wire being composed of at least one metal having a catalytic nature of improving the sensitivity of the metal oxide of said gas composition sensing element to variation in concentration of at least one component of said gas;

whereby said metal wire gives a reinforcing strength to said gas composition sensing element of sheet shape to allow said sensing element to have a reduced thickness thereby providing said sensing element with a high response as well as an increased strength.

10. A gas composition sensor, comprising:

a gas composition sensing element of plate shape consistng of at least one body of sintered metal oxide having an electric resistance value varying in accordance with variation of the composition of a gas to be sensed;

a reticulated metal sheet having a length larger than width of said sensing element and fixedly held in said sensing element to extend across said width of said sensing element in opposite directions such that said reticulated metal sheet bites said sintered metal oxide to provide close adhesion between said sintered metal oxide and said reticulated metal sheet, said reticulated metal sheet serving as a first electrode and fixed at both ends thereof to a housing to fixedly support said sensing element in place for sensing of the gas;

a second electrode having one end thereof fixed to said sensing element to take out, together with said first electrode, and thus permit detection of the electric resistance value indicated by said sensing element when said sensing element is exposed to such gas; and said reticulated metal sheet being composed of at least one metal having a catalytic nature of improving the sensitivity of the metal oxide of said sensing element to variation in concentration of at least one component of said gas;

whereby said reticulated metal sheet gives a reinforcing strength to said sensing element of plate shape to allow said sensing element to have a reduced thickness thereby providing said sensing element with a high response as well as an increased strength.

11. A gas composition sensor as set forth in claim 10, further comprising:

an additional reticulated metal sheet fixedly held to a surface of said sensing element such that said additional reticulated metal sheet bites said surface of said sensing element to provide close adhesion between said additional reticulated metal sheet and said sintered metal oxide, said additional reticulated metal sheet being fixed to said second electrode to provide an electric connection therebetween.

12. A gas composition sensor, comprising:

a gas composition sensing element of plate shape consisting of at least one body of sintered metal oxide having an electric resistance value varying in accordance with variation of the composition of a gas to be sensed;

two reticulated metal sheets fixedly held by two superficial opposite faces of said sensing element such that said metal sheets bite said superficial opposite faces of said sensing element to provide close adhesion between said two reticulated metal sheets and said sintered metal oxide;

two electrodes, each one of them having one end thereof fixed to a respective one of said two reticulated metal sheets to take out and thus permit detection of the electric resistance value indicated by said gas composition sensing element when said sensing element is exposed to such gas; and said two reticulated metal bodies being composed of at least one metal having a catalytic nature of improving the sensitivity of the metal oxide of said gas composition sensing element to variation in concentration of at least one component of said gas;

whereby said two reticulated metal sheets give a reinforcing strength to said gas composition sensing element of plate shape to allow said sensing element to have a reduced thickness thereby providing said sensing element with a high response as well as an increased strength.

13. A gas composition sensor as set forth in claims 1, 8, 10 or 12 wherein said reticulated metal sheet is one selected from a group consisting of a so-called reticulated metal plate, a metal punching plate and metal rods in a reticulated arrangement.

* * * * *